US010827950B2

(12) United States Patent
    Choo et al.

(10) Patent No.: US 10,827,950 B2
(45) Date of Patent: Nov. 10, 2020

(54) POSITION SENSING AND GUIDING SYSTEM

(71) Applicant: CALIFORNIA INSTITUTE OF TECHNOLOGY, Pasadena, CA (US)

(72) Inventors: Hyuck Choo, San Marino, CA (US); Frank L. Brodie, Redondo Beach, CA (US); Robert H. Grubbs, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 334 days.

(21) Appl. No.: 15/061,984

(22) Filed: Mar. 4, 2016

(65) Prior Publication Data

US 2016/0256081 A1    Sep. 8, 2016

Related U.S. Application Data

(60) Provisional application No. 62/128,283, filed on Mar. 4, 2015.

(51) Int. Cl.
    *A61B 5/11*     (2006.01)
    *A61B 5/00*     (2006.01)
    *A61B 5/107*    (2006.01)

(52) U.S. Cl.
    CPC .......... *A61B 5/1116* (2013.01); *A61B 5/1114* (2013.01); *A61B 5/6803* (2013.01);
    (Continued)

(58) Field of Classification Search
    CPC .................................................. A61B 5/1071
    See application file for complete search history.

(56) References Cited

U.S. PATENT DOCUMENTS

5,172,481 A      12/1992  Wiseman et al.
6,032,375 A *    3/2000   Shijo ................. G01C 9/24
                                              33/366.21
(Continued)

FOREIGN PATENT DOCUMENTS

EP          0740131 B1      5/2000

OTHER PUBLICATIONS

International Search Report and Written Opinion dated Jun. 1, 2016, corresponding to PCT/US2016/021068, 8 pages.

*Primary Examiner* — Daniel L Cerioni
*Assistant Examiner* — Raymond P Dulman
(74) *Attorney, Agent, or Firm* — Lewis Roca Rothgerber Christie LLP

(57) ABSTRACT

A position sensing apparatus includes a position sensor, a voltage/current detector, and an alarm. The position sensor is coupled to the body part and includes a capsule, and first and second electrodes. The capsule has an interior volume configured to contain a liquid with a first density, and a contact member having a second density different from the first density. The first and second electrodes are fixed to the capsule to define a sensor meridian that is coupled to a tilt angle of the body part, with each electrode having a distal portion in the interior volume of the capsule, and the distal portions being configured to form a circuit with the liquid or the contact member. The voltage/current detector is configured to detect a change in a state of the circuit, and the alarm is configured to respond to the voltage/current detector.

4 Claims, 12 Drawing Sheets

(52) U.S. Cl.
CPC .......... *A61B 5/6861* (2013.01); *A61B 5/0002* (2013.01); *A61B 5/1071* (2013.01); *A61B 5/746* (2013.01); *A61B 2560/0214* (2013.01); *A61B 2562/168* (2013.01)

(56) References Cited

U.S. PATENT DOCUMENTS

| | | | |
|---|---|---|---|
| 6,453,745 B1* | 9/2002 | Jalkanen | G01C 9/18 33/366.15 |
| 6,505,409 B2 | 1/2003 | Toda et al. | |
| 6,612,157 B2* | 9/2003 | Urano | G01P 15/135 73/65.01 |
| 8,682,607 B2* | 3/2014 | Yamada | G01P 15/135 702/141 |
| 8,725,436 B2* | 5/2014 | Yamada | G01P 13/00 702/57 |
| 2004/0100357 A1 | 5/2004 | Kruse | |
| 2011/0313266 A1 | 12/2011 | Fortsch et al. | |
| 2015/0049002 A1* | 2/2015 | Ishikawa | G02B 27/017 345/8 |
| 2015/0206410 A1* | 7/2015 | Yi | G08B 21/0446 340/573.1 |
| 2019/0021590 A1* | 1/2019 | Francois | G06F 19/00 |

\* cited by examiner

POSITION SENSING AND GUIDING SYSTEM

CROSS-REFERENCE TO RELATED APPLICATION(S)

This application claims priority to and the benefit of provisional U.S. Patent Application No. 62/128,283, filed Mar. 4, 2015, the entire content of which is incorporated herein by reference.

FIELD OF INVENTION

This invention relates to a sensor for sensing the position of a patient's body part, in particular, a change or deviation in an angle of tilt of the patient's head or other body part from an original or preferred angle.

BACKGROUND

Use of intravitreal tamponade with gas or silicone oil is an indispensable method to treat a number of retinal conditions, including rhegmatogenous retinal detachment and macular hole. In the case of retinal detachment, intravitreal gas or silicon oil is used to close and tamponade retinal breaks while a laser- or cryotherapy-induced chorioretinal adhesion forms around these breaks to prevent recurrent detachment. In the operating room, gas or silicone oil is used to fill the vitreous cavity at the time of vitrectomy; intravitreal gas to create a bubble 11 in a patient's eye 14, as shown in FIG. 1A, also can be injected in the office for selected cases of a torn or detached retina 17. Office/out-patient repair of retinal detachment with intraocular gas injection is called pneumatic retinopexy. Injection of intravitreal gas can also be used as an adjunct in the repair of retinal detachment using a scleral buckle, especially in the case of "fishmouthing" of retinal breaks overlying an encircling buckle.

In cases of retinal detachment repair using intraocular gas or silicone oil, the critical principle is to ensure the gas or silicone oil is in contact and completely covers the retinal detachment or break 17, as shown in FIG. 1B. The surface tension created between the oil or gas and the retinal break prevents vitreous fluid from passing through the break and re-accumulating underneath the retina (i.e. causing recurrent retinal detachment). Because retinal breaks can be distributed through the ocular fundus, and because both gas and silicone oil exert a flotation force in an aqueous environment, tamponade of a given retinal break requires that the break be positioned uppermost, as shown in FIG. 1B. For example, if a retinal break is located at the 12 o'clock meridian, then the bubble can be easily positioned over the retinal break with the patient situated in a normal sitting or standing position while holding his head in a vertical position (namely, wherein a longitudinal head meridian M is parallel with the Z axis, as shown in FIG. 2A). Alternatively, if the break is located at the 1:30 o'clock meridian, the patient's head must be tilted with an appropriate angle θ maintained between the Z axis and the vertical head meridian M (as shown in FIG. 2B) to position the bubble over the break. If the head positioning is not correct and the appropriate angle θ is not maintained as medically prescribed, the bubble may not cover ("close") the break, thus preventing retinal re-attachment.

Because it is often difficult for a patient to maintain proper head position (including the proper angle θ or "tilt") to adequately tamponade a retinal break with intravitreal gas, incorrect head positioning can lead to failed retinal detachment surgery. Accurate control of heading positioning can be difficult. Patients often cannot gauge the required tilt of their head to precisely position and/or precisely re-position a bubble over a retinal tear.

An often-used technique to assist the patient is to draw an arrow on an eye patch that is worn by the patient over the subject eye, with the arrow pointing to the meridian of the retinal tear. Then, the patient is instructed to tilt his/her head until the drawn arrow points to 12 o'clock, which effectively positions the bubble correctly relative to the retinal tear so that the flotation force can act on the retinal tear. This technique requires that patients continue to wear the eye patch, which most do not want to do, and to frequently gaze in the mirror to confirm the arrow position.

Because of the difficulty of achieving and maintaining precise head positioning, it is not uncommon for patients to present persistent retinal detachment one day after uncomplicated pneumatic retinopexy. When asked to demonstrate the head position used since surgery, these patients frequently have not positioned properly, resulting in the bubble "missing" the retinal tear. If patients successfully position thereafter, the subretinal fluid resorbs, and the retina reattaches. If, however, the incorrect positioning has resulted in extension of the retinal detachment into the macula, the result can be permanent loss of central vision despite subsequent successful retinal reattachment.

Another clinical situation where intraocular gas is universally used is in the closure of macular holes. Following vitrectomy and removal of the internal limiting membrane, long-acting intravitreal gas in injected into the vitreous cavity and the patient is placed in a prone (face-down) position. Successful closure of a macular hole ordinarily requires seven days of strict face-down positioning. Inadequate positioning compliance causes persistent macular hole and resultant central vision loss.

Following successful closure of a macular hole with long-acting intravitreal gas, the bubble gradually resorbs over an additional period of one to eight weeks, depending on the type of gas injected. Patients do not need to maintain face down positioning during this time; however, they need to avoid supine positioning that causes apposition between the bubble and the lens. Supine positioning, even if allowing only a few hours of contact between the bubble and the lens, can result in visually significant cataract formation.

As important as proper head positioning is with use of intraocular gas or silicone oil, patients are allowed to assume a more comfortable, neutral head position while eating or using the restroom. Normalization of head position for brief periods during the day appears to have no effect on anatomic and visual outcomes; the brief rests do make the rigors of proper head positioning less onerous.

Because use of prolonged intraocular tamponade is dependent on precise positioning while a bubble remains in the eye, improved methods to ensure proper head positioning are essential to optimize surgical and visual outcomes. Accordingly, there is a need for a device that is easy to use, can be portable and comfortably worn by the patient, and yet be effective in helping the patient maintain the proper head position. The device should be easily worn, removed and reworn by the patient without losing accuracy or precision of the proper head position. Moreover, the device should alert the patient when the patient's head position has deviated or changed from the proper head position.

SUMMARY OF THE INVENTION

Some embodiments of the present invention include a head position sensor which structurally and functionally mimics a conventional medical treatment for eye ailments, including a detached, torn or otherwise damaged retina. Much like the intraocular gas or silicone oil used in pneumatic retinopexy, which floats in a patient's eye due to gravity, the head position sensor of the present invention employs gravity to float a bubble or a buoyant member within a capsule of the sensor to sense the head position (including tilt angle) of the patient wearing the head position sensor. With proper initial configuration of the sensor on the patient, the sensor detects in real time a change in the position of the patient's head beyond a threshold tilt angle and helps guide the patient on a proper position or orientation of the head.

In more general aspects, some embodiments of the present invention include a position sensing apparatus for use with a body part of a user, the apparatus having a sensor capsule that is mounted on the body part and thus directly coupled to movement of the body part, the capsule having with a sensor meridian that is responsive to and follows a tilt angle (and changes in the tilt angle) of the body part, wherein the meridian is defined by electrodes that are fixedly mounted to the capsule and configured to form a circuit with one or more conductive elements contained in the capsule depending on the tilt angle of the capsule.

In some embodiments, the position sensing apparatus includes a position sensor, a voltage/current detector, and an alarm. The position sensor is coupled to the body part and includes a capsule, and first and second electrodes. The capsule has an interior volume configured to contain a liquid with a first density, and a contact member having a second density different from the first density. The first and second electrodes are fixed to the capsule to define a sensor meridian that is coupled to a tilt angle of the body part, with each electrode having a distal portion in the interior volume of the capsule, and the distal portions being configured to form a circuit with the liquid or the contact member. The voltage/current detector is configured to detect a change in a state of the circuit, and the alarm is configured to respond to the voltage/current detector.

In some embodiments, the position sensing apparatus for use with a body part of a user, includes a position sensor coupled to the body part, voltage/current detector and an alarm. The position sensor has a capsule, and first and second electrodes. The capsule has an interior volume configured to contain a liquid with a first density, and a member having a second density different from the first density. The first and second electrodes are fixed to the capsule, each electrode having a distal portion in the interior volume. The voltage/current detector is configured to detect a signal when both of the distal portions are in contact with the liquid or the contact member, and the alarm is configured to respond to the voltage/current detector.

In some detailed embodiments, the interior volume is generally spherical.

In some detailed embodiments, the contact member is nonconductive. The contact member may be a bubble. Alternatively, the contact member may be a conductive contact member.

In some detailed embodiments, the position sensing apparatus includes a mounting member configured for mounting on a body part of a patient, and an attachment member configured to attach the position sensor to the mounting member.

In some detailed embodiments, the capsule has an upper portion and a lower portion, wherein the distal portions of the first and second electrodes are located in the upper portion of the capsule, wherein the circuit is in an open state when the first and the second electrodes are both out of contact with a bubble.

In some detailed embodiments, the capsule has an upper portion and a lower portion, wherein the distal portion of the first electrode is in the upper portion and the distal portion of the second electrode is in the lower portion, and wherein the circuit is in a closed state when the distal portions of the first and second electrodes are both out of contact with the bubble.

In some detailed embodiments, the conductive element has a density lesser than a density of the liquid, and wherein the distal portions of the first and second electrodes are in an upper hemisphere of the capsule.

In some detailed embodiments, the conductive element has a density greater than a density of the liquid, and the distal portions of the first and second electrodes are in a lower hemisphere of the capsule.

In some detailed embodiments, each of the distal portions of the first and second electrode is elongated.

In some detailed embodiments, the distal portion of the first electrode is elongated and the distal portion of the second electrode has a ring portion.

In some detailed embodiments, the mounting member includes a head band, a head cap, or an ear cap.

The present invention may also include a head position sensing system that provides for processing of head position data. The system may also provide for transmission or communication of such data to a remote location or device by wireless or cable communication.

In some embodiments, a head position sensing system comprises a position sensor, a controller and an alarm. The position sensor is configured for mounting on a body part of a patient, and having a circuit comprising a first electrode and a second electrode. The electrodes define a sensor meridian configured to follow a tilt angle of the body part and the circuit is configured to change from one circuit state to another circuit state in response to a change in the tilt angle of the sensor meridian and to transmit a signal in response thereto. The controller has a storage with instructions, and a processor configured to process the signal and activate the alarm in accordance with the instructions.

In some embodiments, the circuit states include a closed state and an open state.

In some embodiments, the processor includes circuit state instructions for detecting a change between circuit states, head position instructions for managing head position data, and alarm management instructions for managing activation of the alarm.

In some embodiments, the system includes a wireless interface and/or a cable interface.

In some embodiments, the system includes a user interface.

In some embodiments, the system includes a display screen.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1A:
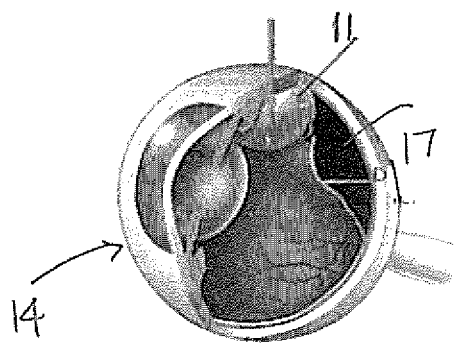
FIG. 1A is an illustration depicting an eye with a damaged retina undergoing pneumatic retinopexy.
Figure 1B:
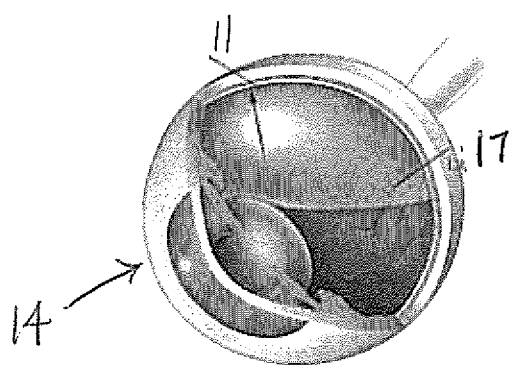
FIG. 1B is the illustration of FIG. 1A, clearly showing an intraocular bubble or silicone oil bubble at the 12 o'clock meridian.
Figure 2A:
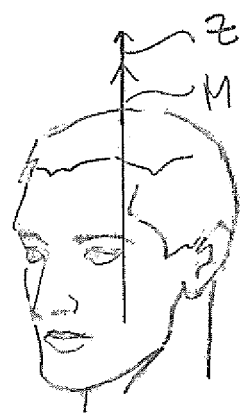
FIG. 2A is an illustration depicting a patient with an upright head position where a head meridian is generally vertically aligned with a Z axis.
Figure 2B:
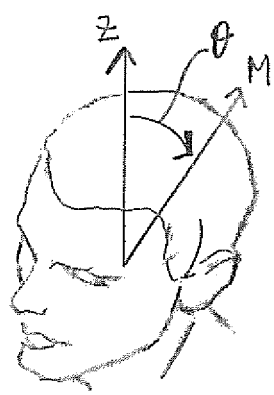
FIG. 2B is an illustration depicting the patient of FIG. 2A with a tilted head position, where the head meridian is at an angle relative to the Z axis.
Figure 3:
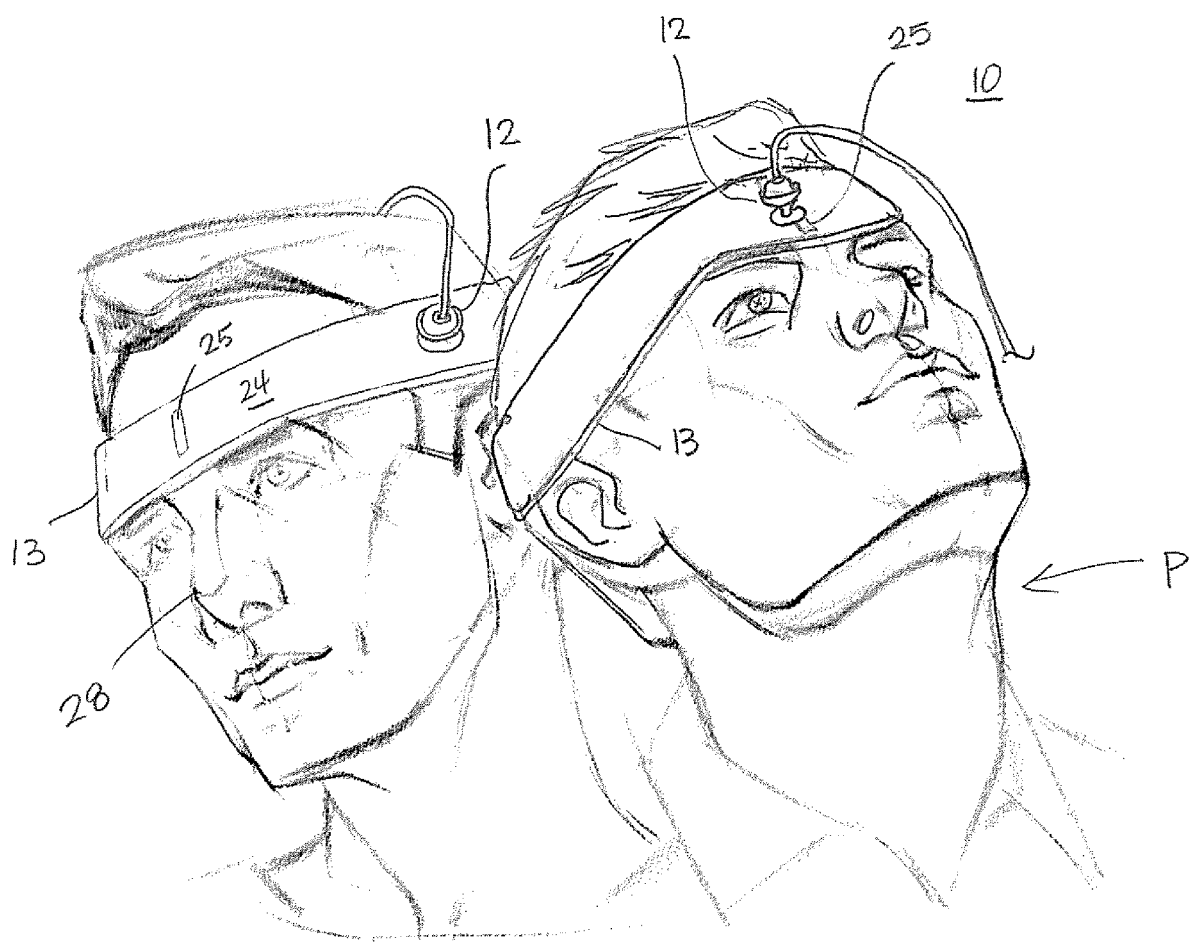
FIG. 3 is an illustration depicting a patient whose head is in different tilt angles.
Figure 4A:
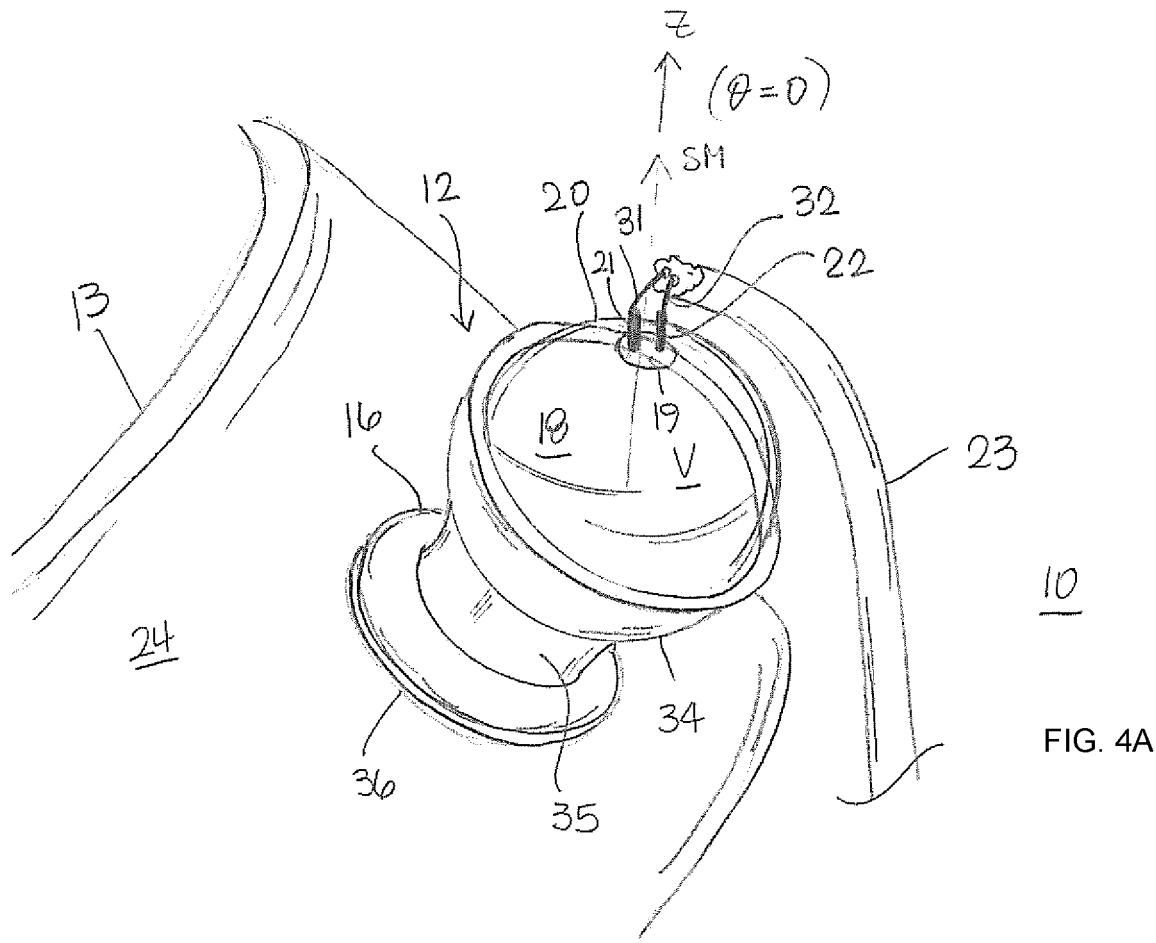
FIG. 4A is a perspective view of a position sensor, a mounting member and an attachment member, according to one embodiment of the present invention.

In some embodiments, a position sensing device 10, as shown in FIG. 3 and FIG. 4A includes a position sensor 12, a mounting member 13 adapted to be worn on a body part (e.g., head 15) of a patient P, and an attachment member 16 configured for attaching the position sensor 12 to the mounting member 13 so that the position 12 and the body part are coupled in movement (including a tilt angle). In the illustrated embodiment of FIG. 4A, the position sensor 12 includes a hollow housing or capsule 20 having an interior cavity defining a volume V that contains an electrically conductive fluid or liquid 18 (for example, water or saline solution) which occupies a predetermined portion lesser than the entirety of volume V so that a contact member, e.g., a fluid (gas or oil) bubble 19, is provided and contained within the cavity of the capsule 20. The contact member has a density different from that of the liquid 18 and is moveable within the interior cavity relative to the capsule 20. The position sensor 12 also includes a first electrode 21 and a second electrode 22, each fixedly mounted to the capsule 20 and each having a distal portion disposed in a the interior cavity and adapted for contact with the contact member. The distal portions of the electrodes are at respective locations that together define a sensor meridian SM of the capsule 20, such that movement or change in the tile angle of the capsule can be defined in terms of movement or a change in the tilt angle of the sensor meridian SM, and vice versa.

Figure 4C:
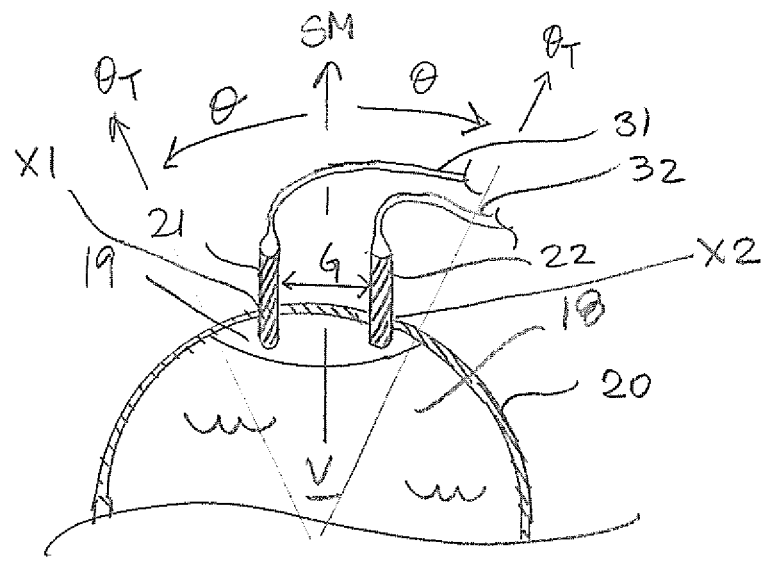
FIG. 4C is a side cross-sectional view of the position sensor for FIG. 4A.
Figure 4B:
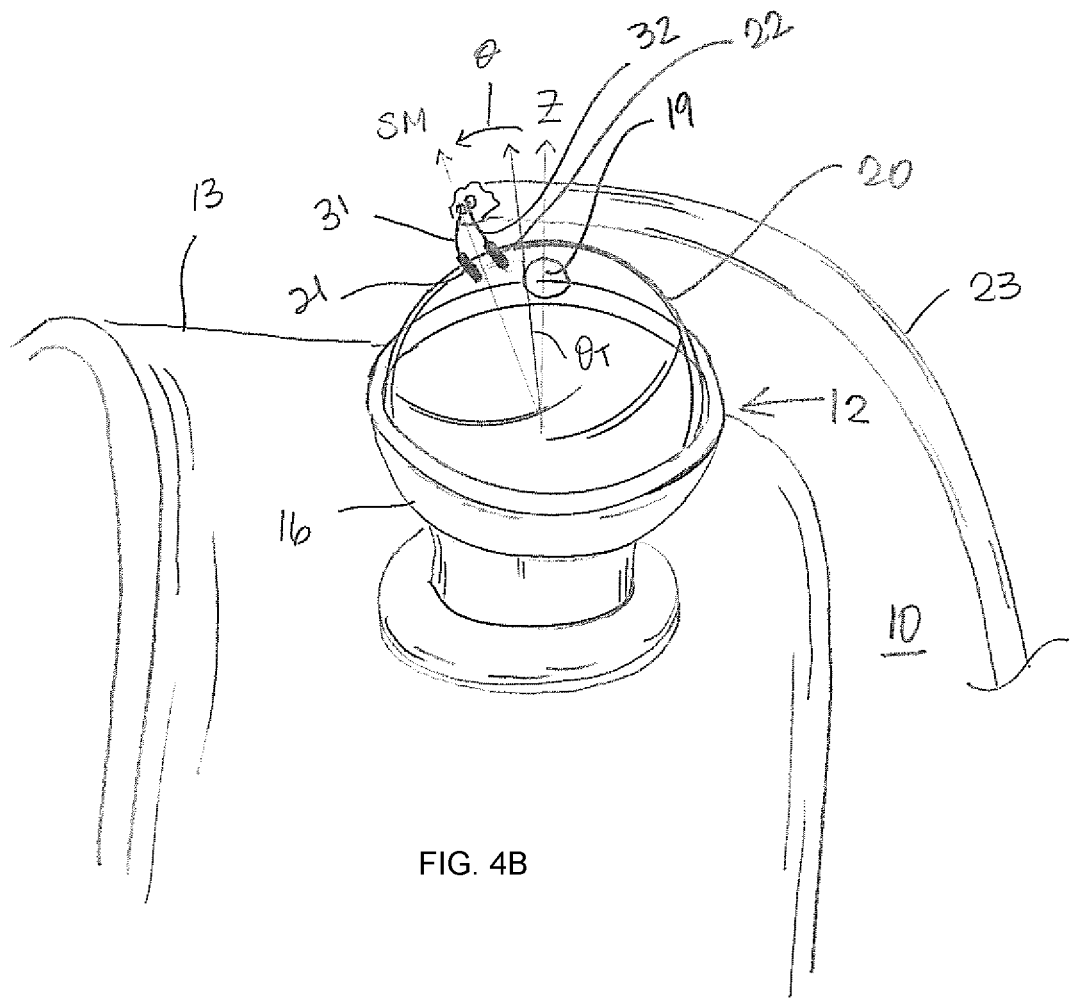
FIG. 4B is a perspective view of the position sensor of FIG. 4A, tilted at an angle.

Each of electrodes 21 and 22 is coupled to a respective of lead wires 31 and 32. With the application of a voltage across a circuit defined by the lead wires 31 and 32, an electrical current can pass across the electrodes 21 and 22 only when the capsule 20 is positioned, angled or tilted (all three wording and variations thereof used interchangeably herein) such that any part of both distal portions of the electrodes are in contact with the conductive fluid 18. Thus, depending on the position of the capsule 20, the circuit through the electrodes 21 and 22 and the lead wires 31 and 32 is open when the distal portion of either electrode is surrounded by or "in contact" with the bubble 19, as shown in FIG. 4A, and closed when any part of the distal portions of both electrodes are in contact with the fluid, as shown in FIG. 4B. The lead wires 31 and 32 and the proximal portions of the electrodes 21 and 22 outside of the capsule 20 may be surrounded by a protective tubing 23 (whose distal end is shown partially broken away).

In accordance with feature(s) of the present invention, the circuit is in (or brought into) one state where the sensor meridian SM and the Z axis are generally aligned and an angle θ therebetween is equal to or less than a threshold angle $\theta_T$ (see FIG. 4A), and the circuit is in (or brought into) another state where the angle θ between the sensor meridian SM and the Z axis is greater than a threshold angle $\theta_T$ (see FIG. 4B). As shown in FIG. 4C, the threshold angle $\theta_T$ defines the "sensitivity" of the sensor, and is dependent on a plurality of configuration parameters of the sensor, including, for example, a separation distance or gap G between the distal portions of the electrodes 21 and 22. In that regard, it is understood that the distal portions of the first and second electrodes 21 and 22 are disposed at a first location X1 and a second location X2 (different from the first location X1) in or on the capsule 20, respectively, so that each can independently come into contact with the conductive fluid 18 or the contact member depending on the tilt of the capsule 20.

Other configuration parameters that may define sensitivity include various absolute and/or relative parameters of and/or between the contact member and the distal portions of the electrodes 21 and 22, including, for example, the size or volume of the bubble 19 (or the amount of volume of the conductive fluid 18) in relation to the volume of the cavity of the capsule 20, and the depth of projection and the size/diameter of each distal portion of the electrodes in the cavity of the capsule.

Figure 6A:
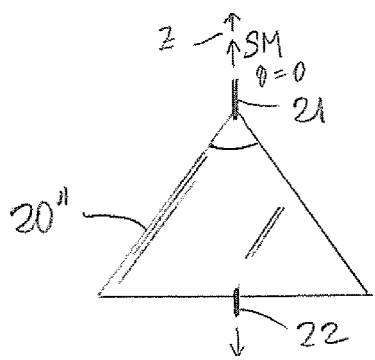
FIGS. 6A, 6B and 6C are side views of an upright triangular capsule, at different tilt angles.
Figure 6B:
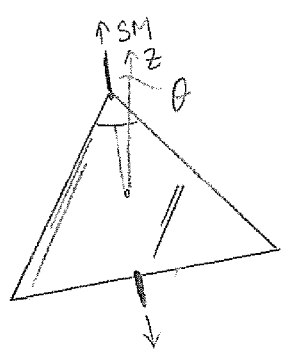
Figure 6C:
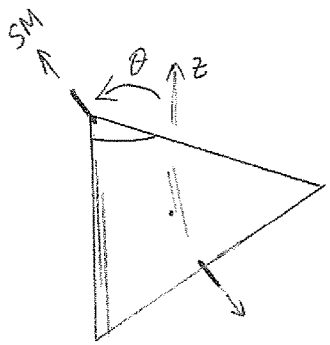
Figure 7A:
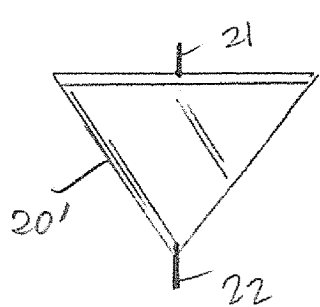
FIG. 7A, FIG. 7B and FIG. 7C are side views of an upside down triangular capsule, at different tilt angles.
Figure 7B:
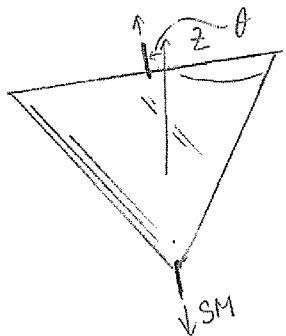
Figure 7C:
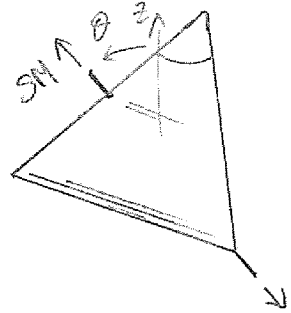
Figure 5A:
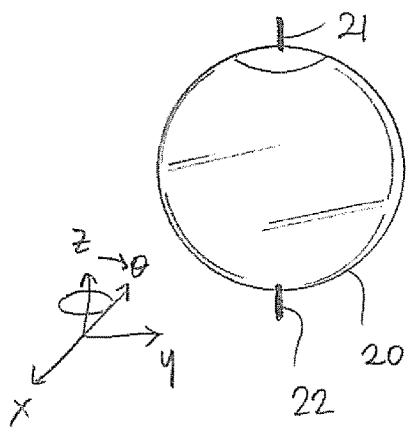
FIG. 5A, FIG. 5B and FIG. 5C are side views of a spherical capsule, at different tilt angles.
Figure 5B:
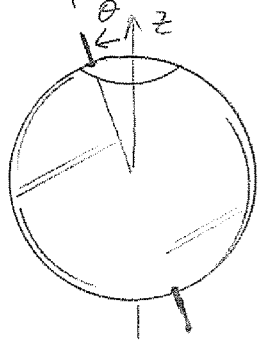
Figure 5C:
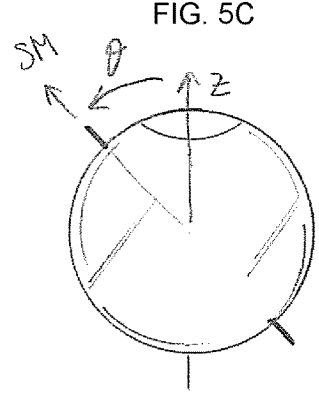

Another configuration parameter is the shape of the capsule 20, in particular, the shape of its interior cavity. In the illustrated embodiment of FIG. 4A and FIG. 4B, the interior cavity of the capsule 20 has a spherical configuration, with symmetry about three orthogonal axes x, y and z. As such, the sensor 12 is equally sensitive for all values (or ranges) of angle θ, as shown in FIG. 5A, FIG. 5B and FIG. 5C. However, with a nonspherical configuration, the sensor has different sensitivity for different values of angle θ. With reference to FIG. 6A, FIG. 6B and FIG. 6C, a capsule 20' with an interior cavity having an upright triangular configuration which tends to confine the contact element in its uppermost corner and thus has a lesser sensitivity for at least a lower range of angle θ, whereas a capsule 20" with an interior cavity having an inverted triangular configuration allows greater movement of the contact element and thus has a greater sensitivity for at least the same lower range of angle θ, as shown in FIG. 7A, FIG. 7B and FIG. 7C. It is understood that sensitivity is decreased where the region of the cavity near the uppermost sensor meridian SM is decreased relative to a spherical configuration, as shown in FIG. 6A, FIG. 6B and FIG. 6C, and that sensitivity is increased where the region of the cavity near the uppermost sensor meridian SM is increased relative to a spherical configuration, as shown in FIG. 7A, FIG. 7B and FIG. 7C. Accordingly, different sensitivities can be achieved by purposeful configuration of the cavity.

The capsule 20 may be constructed of any nonconductive material with sufficient rigidity to maintain a predetermined shape notwithstanding the pressure of the contained fluid and the force of gravity acting thereon. Suitable materials, include, for example, plastics, polymers, resins, ceramics, glasses and rubbers. The material may be opaque, although transparent material permits a user to visually examine features, movements and states of the bubble 19, including, for example, the location of the bubble 19 relative to the electrodes 21 and 22, and the amount or volume of fluid 18 in the cavity, and the size or volume of the bubble 19.

Figure 8:
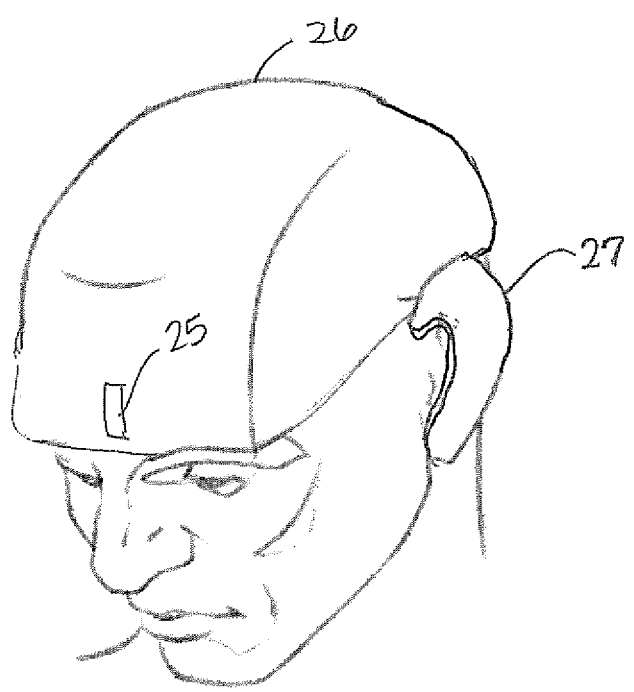
FIG. 8 is an illustration of a patient wearing a mounting member on his head and on his ear, in accordance different embodiments of the present invention.

In some embodiments, the sensor 12 is adapted to be worn on the patient's head via the mounting member 13. In the illustrated embodiment of FIG. 3 and FIG. 4A, the mounting member 13 includes a head band that encircles the circumference of the patient's head 15 above the ears and is thus configured to be worn around the crown of the patient's head. The head band may be flexible or semi-rigid, and adjustable to fit the patient's head. The mounting member 13 has an outer surface 24 that is visible or exposed when the member 13 is worn on the patient's head. On the outer surface 24 is one or more visual and/or tactile orientation indicia 25 that may be aligned with one or more features of the patient's head (or body), for example, the nose 28. The outer surface 24 also provides a suitable surface for releasable attachment of the attachment member 16, as described below in further detail. In other embodiments, the mounting member 13 may cover more portions or a different portion of the patient's head and include a head cap or helmet 26 or an ear cap 27, as shown in FIG. 8.

Figure 4D:
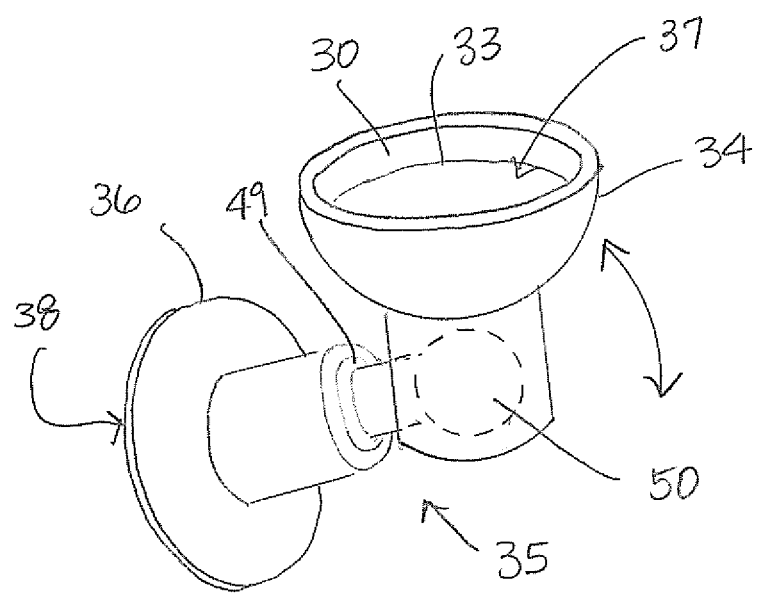
FIG. 4D is a perspective view of a mounting member and an attachment member, in accordance with another embodiment of the present invention.

With reference to FIG. 4A, the attachment member 16 has a first portion 34, a second portion or base 36, and a connecting portion 35 therebetween. The connecting portion 35 may include a generally rigid stem or a joint that allows adjustability in extension distance and/or one or more angles between the attachment portions 34 and 36. In the embodiment of FIG. 4D, the connecting portion includes a telescoping portion 49 and a ball and socket connection 50 which are configured to hold any number of configurations set by the user.

In some embodiments, the first attachment portion 34 has a recessed region 37 that is configured to receive at least a portion of capsule 20 of the sensor 12. In the illustrated embodiment, the recessed region 37 includes a semi-spherical cup portion with an inner surface 30 defining a concavity that generally corresponds to the convexity of the capsule 20 so as to allow the recessed region 37 to hold or support the capsule 20. The inner surface 30 may include a fastener member 33, for example, a coating of adhesive or one of loop and hook members (with the other loop and hook members being affixed to an outer surface of the capsule 20), for affixing the capsule 20 to the cup portion 37 in a multitude of orientation.

The attachment portion or base 36 includes on its underside an attachment surface 38, including a generally flat surface, suitable for contact with the outer surface 24 of the mounting member 13. The base 38 and the outer surface 24 are configured for fixed or releasable attachment to each other, including releasable attachment. The base 38 and the outer surface 24 may be configured for attachment to each other by one or more coatings of adhesive, respective hook and loop fasteners, or the like.

The present invention includes alternate embodiments that provide different circuit configuration for the sensor 12. In the illustrated embodiment of the sensor 12 of FIG. 4A and FIG. 4B, the distal portions of electrodes 21 and 22 are both configured as elongated rods and are both positioned at the uppermost region of the capsule 20, near each other in a common (upper) hemisphere and near a common (upper) end of the sensor vertical meridian SM. As shown in FIG. 4A, the circuit is "open" when the distal portions of both electrodes 21 and 22 of the sensor 12 are surrounded by and "in contact" with a nonconductive floating contact member or bubble 19, and not in contact with the conductive fluid 18. Thus, the circuit is open when the angle θ=0 or less than or equal to the threshold angle $\theta_T$. In contrast, where the capsule has been tilted such that the angle θ is greater the threshold angle $\theta_T$, as shown in FIG. 4B, the circuit is "closed."

Figure 9A:
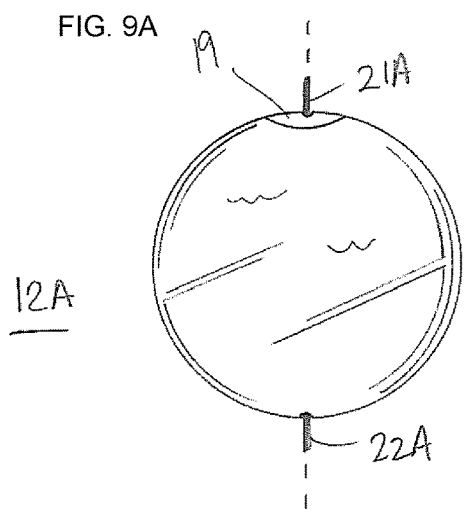
FIG. 9A and FIG. 9B are side views of a position sensor with a circuit configuration, according to a first alternate embodiment.
Figure 9B:
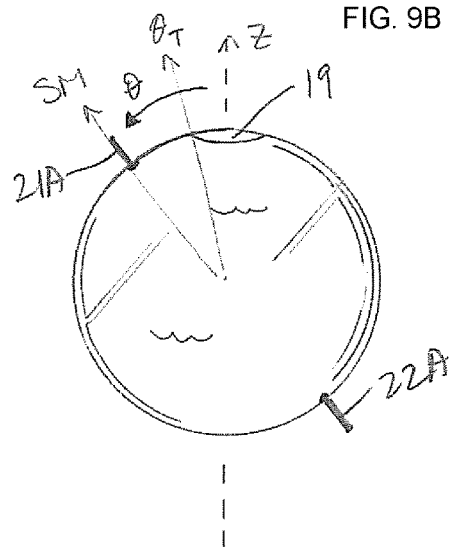

In the illustrated alternate embodiment of a sensor 12A of FIG. 9A and FIG. 9B, the distal portions of the first electrode 21A and the second electrode 22A are both generally aligned with the sensor vertical meridian SM but they are different hemispheres and are diametrically opposite of each other. As shown in FIG. 9A, the circuit is "open" when the distal portion of electrode 21A of the sensor 12A is surrounded by and "in contact" with a nonconductive floating contact member or bubble 19. Thus, the circuit is open when the angle θ=0 less than or equal to the threshold angle $\theta_T$. As shown in FIG. 9B, the circuit is closed when the capsule has been tilted such that angle θ is greater the threshold angle $\theta_T$.

Figure 10A:
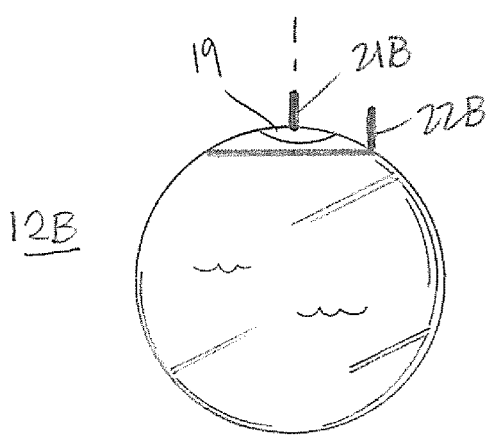
FIG. 10A and FIG. 10B are side views of a position sensor with a circuit configuration, according to a second alternate embodiment.
Figure 10B:
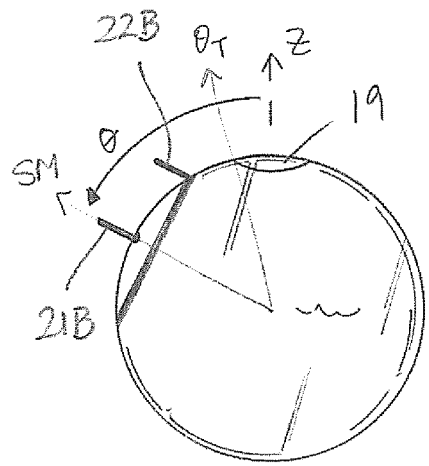

In the illustrated alternate embodiment of FIG. 10A and FIG. 10B, sensor 12B is configured with electrodes 21B and 22B, both positioned in the uppermost region of the capsule 20, near each other in a common hemisphere and near a common end of the sensor vertical meridian SM, but whereas the first electrode 21B is configured as an elongated rod, the second electrode 22B is configured as a ring surrounding and concentric with the first electrode 21B. The second electrode 22B is positioned below a nonconductive floating contact member or bubble 19 so that only the first electrode 21A is out of contact with the conductive fluid when the angle θ=0, and only comes in contact with the conductive fluid when the angle θ is greater than the threshold angle $\theta_T$. Accordingly, for sensor 12B, the circuit is open when the angle θ=0, or less than or equal to the threshold angle $\theta_T$, and the circuit is closed when the angle θ is greater the threshold angle $\theta_T$, as shown in FIG. 10B.

Figure 11A:
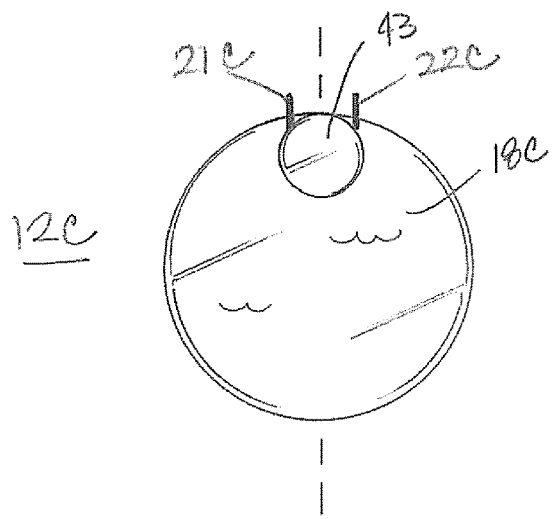
FIG. 11A and FIG. 11B are side views of a position sensor with a circuit configuration, according to a third alternate embodiment.
Figure 11B:
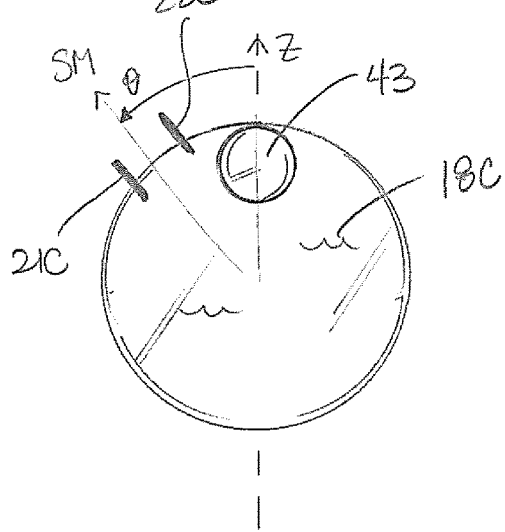

In the illustrated alternate embodiment of FIG. 11A and FIG. 11B, sensor 12C is configured with electrodes 21C and 22C both positioned in the uppermost region of the capsule 20, near each other in a common hemisphere and near a common end of the sensor vertical meridian SM. However, in contrast to the sensor 12 of FIGS. 4A and 4B, the cavity of the sensor 12C contains a nonconductive fluid 18C, and a conductive floating contact member 43 whose density is less than the density of the fluid 18C so that it floats in the fluid 18C. The member 43 is illustrated as a sphere but it is understood that the member 43 may adopt other suitable configurations so long as it can contact both the electrodes 21C and 22C when the angle $\theta=0$. Accordingly, for sensor 12C, the circuit is open when the angle $\theta=0$, and the circuit is closed when the angle $\theta \neq 0$, as shown in FIG. 11B, particularly where the member 43 is spherical so that it can readily be dislodged from contact with both electrodes 21C and 22C.

Figure 12A:
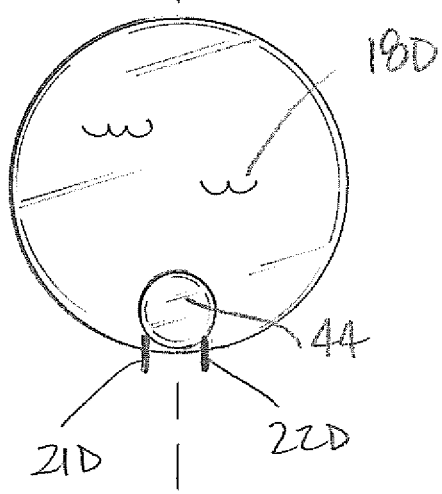
FIG. 12A and FIG. 12B are side views of a position sensor with a circuit configuration, according to a fourth alternate embodiment.
Figure 12B:
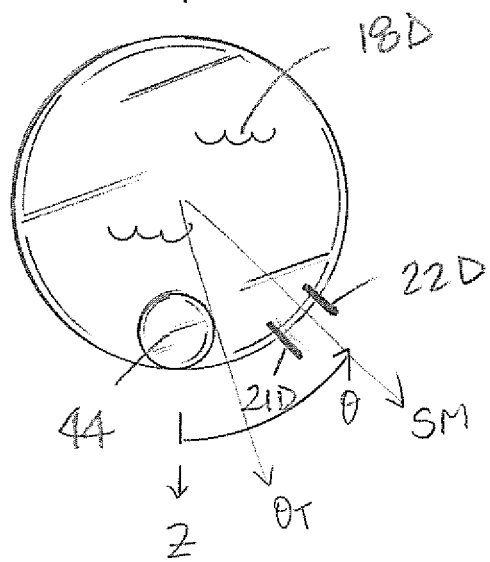

In the illustrated alternate embodiment of FIG. 12A and FIG. 12B, sensor 12D is configured with electrodes 21D and 22D both positioned in the lowermost region of the capsule 20, near each other in a common hemisphere and near a common end of the sensor vertical meridian SM. However, in contrast to the sensor 12C of FIGS. 11A and 11B, the cavity of the sensor 12C contains a nonconductive fluid 18D, and a conductive sinking contact member 44 whose density is greater than the density of the fluid 18D so that it sinks in the fluid 18D. The member 44 is illustrated as a sphere but it is understood that the member 44 may adopt other suitable configurations so long as it can contact with both the electrodes 21D and 22D when the angle $\theta=0$. Accordingly, for sensor 12D, the circuit is open when the angle $\theta=0$, and the circuit is closed when the angle $\theta \neq 0$, as shown in FIG. 12B.

Figure 13:
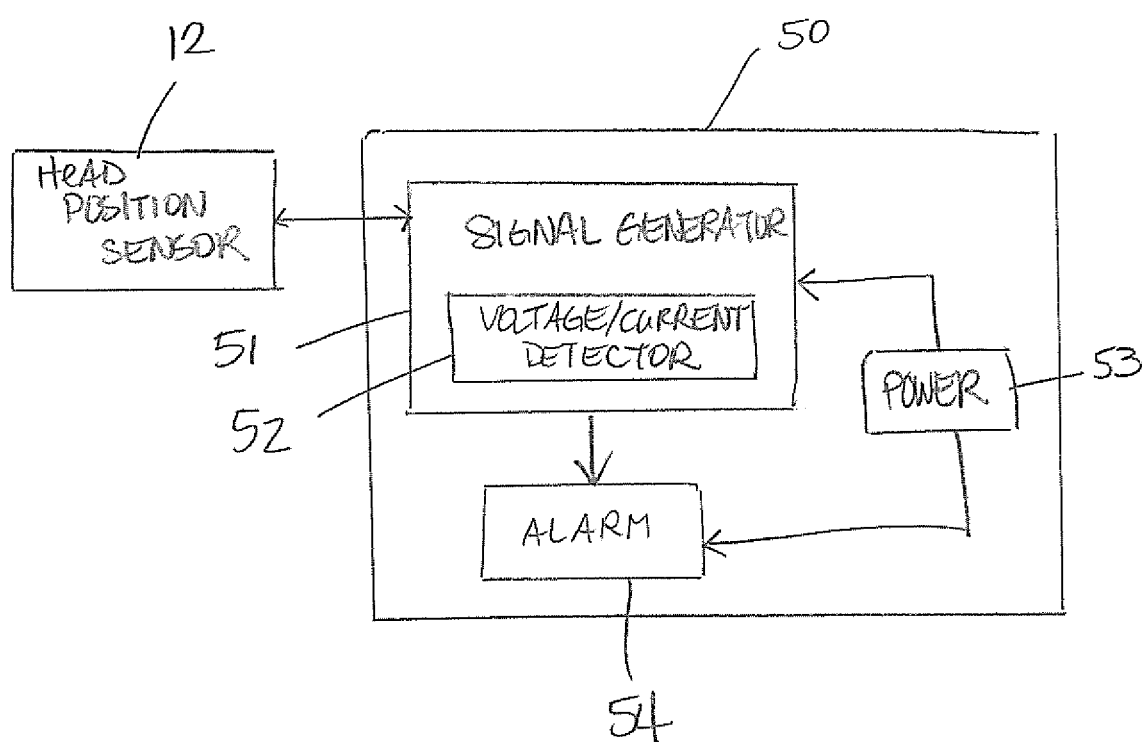
FIG. 13 is a block diagram of a position sensing apparatus, in accordance with an embodiment of the present invention.

In some embodiments, a head positioning apparatus 50 of the present invention includes the sensor 12, and a housing 50 containing a signal generator 51 including a voltage/current detector 52, an alarm 54 responsive to the signal generator 51 and a power source 53 for the apparatus configured to provide a current to the signal generator 51, as shown in FIG. 13. When the electrode circuit of the sensor 12 receives DC power, the voltage/current detector 52 is configured to detect a current flowing from the sensor 12 only when the electrode circuit is closed. The signal generator 51 is configured to activate the alarm 54 only when the electrode circuit is closed. In some embodiments, the signal generator 51 can be configured to activate the alarm 54 only when the electrode circuit is open.

Figure 14:
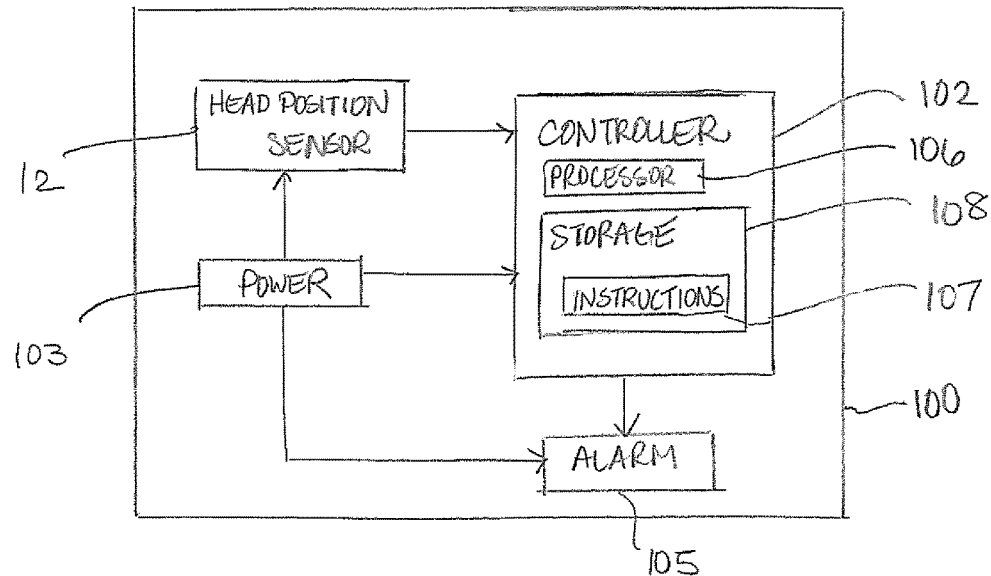
FIG. 14 is a block diagram of a position sensing system, in accordance with an embodiment of the present invention.
Figure 15:
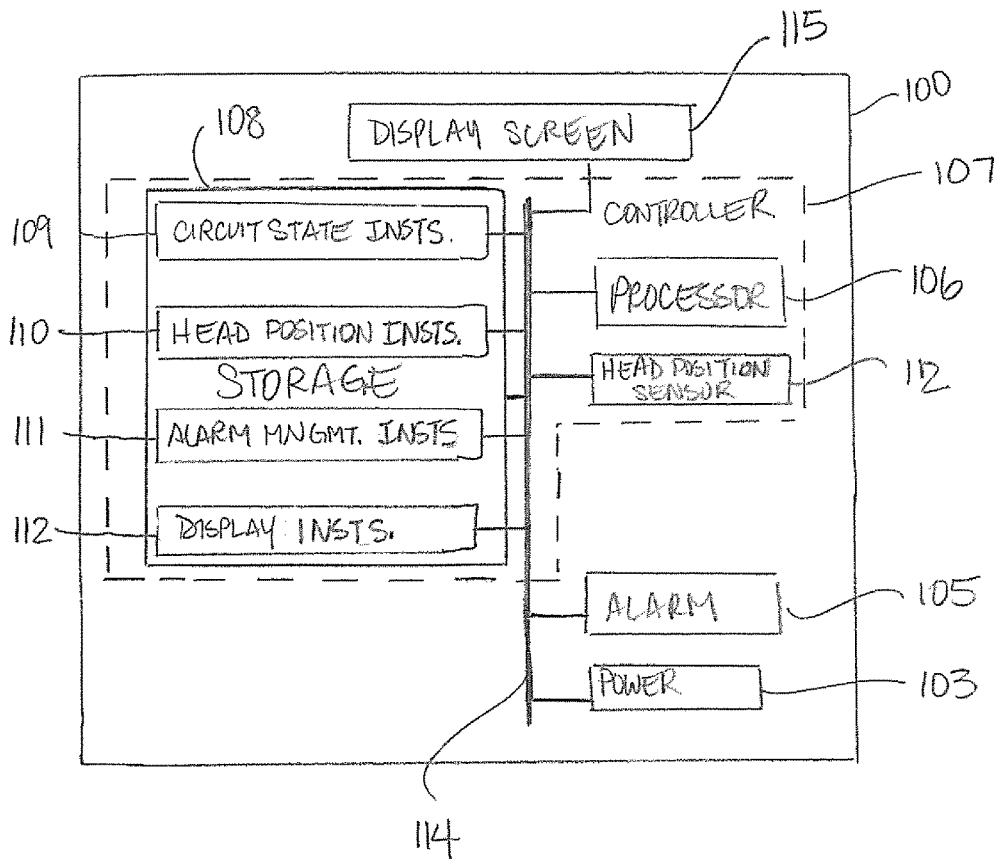
FIG. 15 is a block diagram of a position sensing system, in accordance with another embodiment of the present invention.

In some embodiments, a head positioning system 100 of the present includes the head position sensor 12 and other device components which may be in the form of instructions, storage, and glue instructions, one or more processors, microelectronics, and interfacing circuitry. In some embodiments, the other device components include at least a controller 102, a power source 103, and an alarm 105, as shown in FIG. 14. The power source 103 may be AC- or DC-based (battery). In some embodiments, the controller 102 includes at least one processor 106, storage (e.g., memory) 108 (with instructions 107), as shown in FIG. 15. Instructions 107 may include circuit state detection instructions 109, head position instructions 110 and alarm management instructions 111. The circuit state detection instructions 109 include instructions that are configured to, e.g., process the current and/or voltage of the sensor 12 in sensing the states of the circuit between the electrodes, for example, whether the circuit is closed and or open.

The head position instructions 110 is configured to, e.g., process circuit state data produced by the circuit state detection instructions, so as to quantify circuit state change data and produce identifiable head position data associated with changes in the angle $\theta$ of the sensor 12. The head position instructions 110 may also function to detect selected head positions (e.g., certain values of angle $\theta$), or changes in head positions, and/or whether one or more head position treatment regimen has been completed.

The alarm management instructions 111 include instructions that are configured to, e.g., activate the alarm when the circuit is open, closed or its state changes, and when a time period for a treatment session has ended. In that regard, the alarm management instructions 111 is configured to be responsive to data produced by the head position instructions 110. The alarm management instructions 111 can also interface with a timekeeping module (e.g., clock, calendar, time zone, etc.) and can trigger activation of the alarm. The alarm can be in the form of an audible alarm or a non-audible alarm provided on the mounting member 13 or elsewhere. The non-audible alarm can provide alarm by a light or a vibration. The light can be provided by a light source. The vibration can be produced by a vibration motor.

Figure 16:
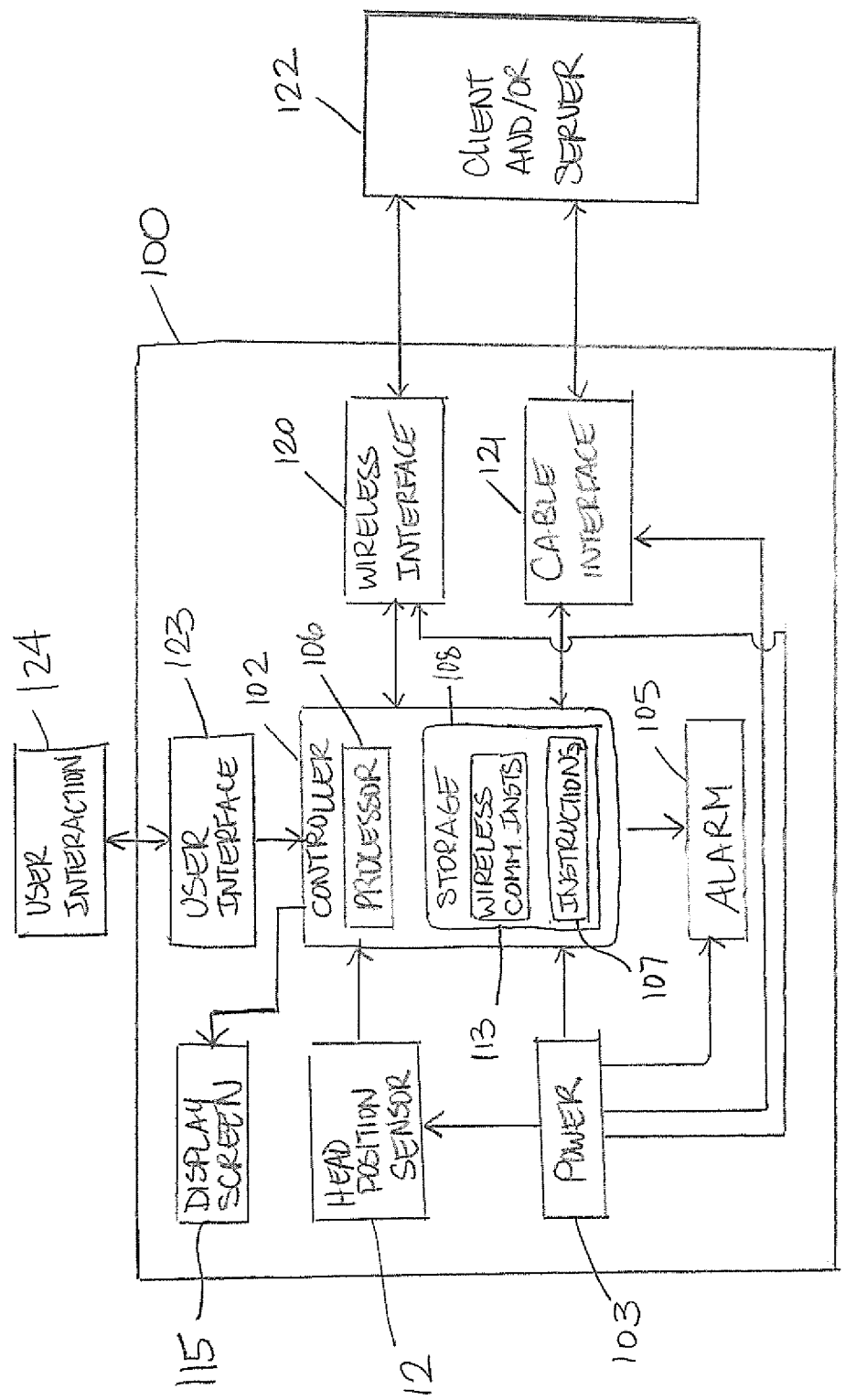
FIG. 16 is a block diagram of a position sensing system, in accordance with yet another embodiment of the present invention.

In some embodiments, the system 100 further includes a wireless interface 120, a cable interface 121, and a user interface 123, as shown in FIG. 16. The user interface 123 may be configured to receive user interaction 124 that is in the form of physical contact (e.g., without limitation, tapping, sliding, rubbing, multiple taps, gestures, etc.). Alternately, or in addition to, the user interface 124 may be configured to receive user interaction that is in the form of nonphysical contact (e.g., without limitation, proximity sensors, button presses, touch sensitive screen inputs, graphical user interface inputs, voice inputs, sounds inputs, etc.). The system 100 can communicate with a client and/or server 122 using a cable connection, e.g., a USB port, or a wireless connection, which is enabled by wireless communication instructions 113 (see FIG. 16). The wireless communication instructions can be in the form of a circuit having radio communication capabilities. The radio communication capabilities can be in the form of a Wi-Fi connection, a Bluetooth connection, a low-energy Bluetooth connection, or any other form of wireless tethering or near field communication.

The wireless communication instructions 113 are configured for communication of the head position system 100 with another computing device by way of a wireless signal. The wireless communication instructions can interface with the controller for transferring head position data, which may be in the form of head position data or processed head position data, stored in the storage 108 to the computing device.

In some embodiments, the processor 106 of the controller 102 functions in conjunction with the various instructions components. The processor 106 can, in some embodiments, provide the functionality of any one or all of the instructions components. In other embodiments, multiple chips can be used to separate the processing performed by any one of the instructions components and the processor. It is understood that "instructions" as used herein may be software, hardware, or combinations thereof. The storage 108 (and instructions 107), the processor 106, the sensor 12, the alarm 105 and power 103 can communicate with each other via a bus 114 (see FIG. 15). The storage 108 is in communication with the bus 114 for providing storage of the head position data processed or tracked by the system 100. Battery may be provided for providing power to the system.

In some embodiment, the system 100 further includes a display screen 115, as shown in FIG. 15 and FIG. 16. The display screen can include, for example, liquid crystal display (LCD) screens, light emitting diode (LED) screens, organic light emitting diode (OLED) screens, plasma display screens, etc. The display screen 115 may be provided on a wearable device, for example, a device clippable to clothing or a wrist cuff. The wearable device may include the alarm 105, the display screen 115 and a button that can be pressed to activate the display screen, navigate to various metrics displayed on the screen, or to turn off the screen.

Figure 17:
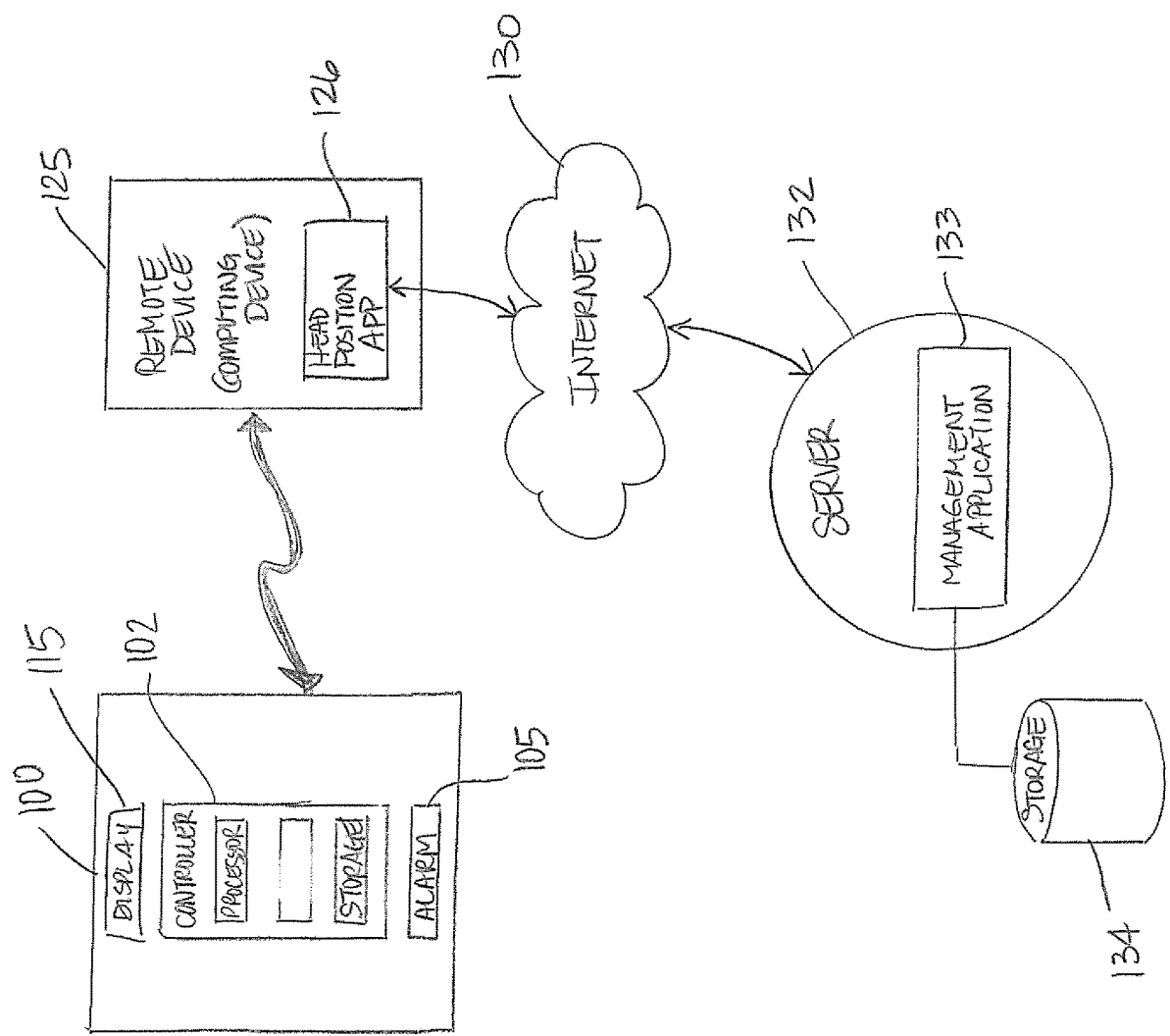
FIG. 17 is a block diagram of a position sensing system in communication with a remote device, in accordance with an embodiment of the present invention.

FIG. 17 illustrates an embodiment of the system 100 in communication with a remote device 125. Remove device 125 is a computing device that is capable of communicating wirelessly with the system 100 and with the Internet 130. Remote device 125 can support installation and execution of applications. Such applications may include head position sensing application 126 which can be downloaded from a server 132. The server 132 can be a specialized server or a server that provides applications to devices, such as an application store. Once the head position sensing application 126 is installed in the remote device 125, the remote device can communicate or be set to communicate with the system 100. The remove device 125 can be a smart phone, a handheld computer, a tablet computer, a laptop computer, a desktop computer, or any other computing device capable of wirelessly interfacing with the system 100 and the Internet 130.

The remote device 125 communicates with the system 100 by way of radio signals, as described above. The remove device 125 can also communicate with the Internet 130 using an Internet connection, which may include cellular communications, wireless connections such as Wi-Fi, and combinations thereof (such as connections to switches between different types of connection links). The remote device 125, as described above, can be a smartphone or tablet computer, or any other type of computing device having access to the Internet and with capabilities for communicating with the system 100. As such, it is understood that the head position application 126 may also provide alarm and display functions in lieu of or in addition to the alarm 105 and display screen 115.

The server 132 is interfaced with the Internet 130 and the server 132 can function to provide access to a patient or a user to view the patient's data associated with the system 100. In some embodiments, the patient data includes the tracked head position sensing data which is processed to identify a plurality of metrics associated with the head position sensing data. The patient data viewable by the patient or a user (such as a treating physician's office) can include metrics such as number of treatment sessions, duration of each treatment session, number of circuit state changes, number of alarm activation, etc.

The metrics are shown in various graphical user interfaces of a website enabled by the server 132. The website can include various pages with graphical user interfaces for rendering and displaying the various metrics for view by the patient or the user. In some embodiments, the website can also include interfaces that allow for data entry and configuration by the patient or user.

The preceding description has been presented with reference to presently preferred embodiments of the invention. It is understood that the present invention may be used for sensing position or angle, or changes in position or angle, of any one or more body parts of a patient. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

According to one embodiment, any instructions or application may be implemented via computer program instructions stored in memory and executed by a processor in the system 100. Of course, the instructions and/or application may also be implemented via hardware, firmware (e.g. ASIC), or any combination of hardware, firmware, and software as will be apparent to a person of skill in the art.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A system for improving a patient's head position compliance after treatment of a location in an eye with intraocular gas or oil, the system comprising:
   a head position sensor configured for mounting on the head of the patient and comprising:
      a capsule having an interior volume configured to contain a liquid with a first density,
      a contact member having a second density different from the first density, and
      a circuit comprising:
         a first electrode, and
         a second electrode, the first and second electrodes defining a sensor meridian within the capsule, the sensor meridian configured to follow a tilt angle of the head,
         the circuit configured to change from a first circuit state to a second circuit state in response to a change in the tilt angle of the head,
            the first circuit state being indicative of at least one of the first and second electrodes being in contact with the contact member, and
            the second circuit state being indicative of both of the first and second electrodes being in contact with the liquid;
   an audio, visual or vibratory alarm responsive to a controller;
   the controller having a storage with circuit state detection instructions, head position instructions, alarm management instructions, and a processor,
      the circuit state detection instructions comprising instructions to detect whether the circuit is in the first circuit state or the second circuit state, the head position instructions being responsive to the circuit state detection instructions and comprising instructions to detect the tilt angle of the head, changes in the tilt angle of the head, and/or whether a prescribed head position treatment regimen has been completed, the alarm management instructions being responsive to the head position instructions and comprising instructions to:

activate the alarm only when the circuit is in one of the first circuit state and the second circuit state but not in the other of the first circuit state and the second circuit state, and/or the circuit changes from one of the first circuit state and the second circuit state to the other of the first circuit state and the second circuit state, and/or when a predetermined time period for the prescribed head position treatment regimen has ended, the controller, responsive to the circuit state detection instructions, the head position instructions, and the alarm management instructions, being configured to activate the alarm when the tilt angle of the head moves beyond a threshold deviation from a treatment tilt angle in the prescribed head position treatment regimen, the treatment tilt angle in the prescribed head position treatment regimen being configured to mimic the location in the eye of the treatment with the intraocular gas or oil.

2. The system of claim 1, wherein one of the first and second circuit states is a closed state and the other of the first and second circuit states is an open state.

3. The system of claim 1, further comprising at least one selected from a group consisting of a wireless interface, a cable interface, a user interface and a display screen.

4. The system of claim 1, wherein each of the first electrode and the second electrode has a distal portion in the interior volume, the distal portions being configured to form the circuit with one selected from a group consisting of the liquid and the contact member.

* * * * *